United States Patent [19]

Kameswaran

[11] Patent Number: 5,659,046
[45] Date of Patent: Aug. 19, 1997

[54] METHOD FOR THE PREPARATION OF 2-PERFLUOROALKYL-3-OXAZOLIN-5-ONE

[75] Inventor: Venkataraman Kameswaran, Princeton Junction, N.J.

[73] Assignee: American Cyanamid Company, Madison, N.J.

[21] Appl. No.: 175,822

[22] Filed: Dec. 30, 1993

[51] Int. Cl.$^6$ ............................................... C07D 263/42
[52] U.S. Cl. ............................................................ 548/228
[58] Field of Search ............................................... 548/228

[56] References Cited

U.S. PATENT DOCUMENTS

| 5,010,098 | 4/1991 | Brown et al. | 514/426 |
|---|---|---|---|
| 5,028,256 | 7/1991 | Martin | 549/370 |
| 5,030,735 | 7/1991 | Addor et al. | 548/531 |
| 5,118,816 | 6/1992 | Doehner, Jr. et al. | 548/531 |
| 5,426,225 | 6/1995 | Kameswaran | 564/212 |
| 5,446,170 | 8/1995 | Kameswaryn | 548/517 |
| 5,453,508 | 9/1995 | Knapp | 548/228 |

OTHER PUBLICATIONS

Martin, W.L.; Owens, D.A.; Comer, W.T.; Deitchman, D.; Ferguson, H.C. Seidehamel, R.J.; Young, J.R. Journal of Medicinal Chemistry, 1973, 16, 901.
Poupaert et al. Chem. Abstr. vol. 78 entry 43335 (1972).
Hawley "Condensed Chemical Dictionary" 10th Ed. Van Nostrand, N.Y., pp. 13–14, 11 (1981).

*Primary Examiner*—Donald G. Daus
*Attorney, Agent, or Firm*—John W. Hogan, Jr.

[57] ABSTRACT

There is provided a method for the preparation of a 2-perfluoroalkyl-3-oxazolin-5-one compound comprising reacting an aminonitrile with a perfluoroacylating agent in the presence of a solvent to form a perfluoroalkanoyl aminonitrile intermediate and cyclizing the intermediate in the presence of an acid and at least one molar equivalent of water.

17 Claims, No Drawings

METHOD FOR THE PREPARATION OF 2-PERFLUOROALKYL-3-OXAZOLIN-5-ONE

BACKGROUND OF THE INVENTION

Arylpyrrole carbonitrile compounds and derivatives thereof are highly effective insecticidal, acaricidal and nematocidal agents. In particular 2-aryl-5-trifluoromethylpyrrole-3-carbonitrile compounds and their derivatives have been found to have a broad spectrum of activity at very low rates of application with effectiveness against resistant species. U.S. Pat. No 5,030,735 describes methods to prepare said pyrrole compounds on a manufacturing scale and includes the 1,3-dipolar cycloaddition of the appropriate 3-oxazolin-5-one with 2-chloroacrylonitrile. Heretofore the 3-oxazolin-5-one key intermediate has been prepared through the appropriate phenylglycine compound in a 4 step synthetic route starting from the preceding aminonitrile.

It is an object of this invention to provide a facile and efficient synthesis of 2-perfluoroalkyl-3-oxazolin-5-one in 2 steps from the aminonitrile precursor.

It is a further object of this invention to provide a convenient source of a key intermediate in the manufacture of insecticidal, acaricidal and nematocidal arylpyrrole compounds.

SUMMARY OF THE INVENTION

There is provided a method for the preparation of a 2-perfluoroalkyl-3-oxazolin-5-one compound of formula II

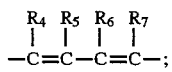

(II)

wherein n is an integer of 1, 2, 3, 4, 5, 6, 7 or 8;

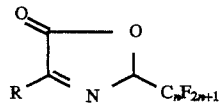

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure —OCH$_2$O—, —OCF$_2$O— or —CH=CH—CH=CH— with the proviso that at least one of L, M and Q must be other than hydrogen;

$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

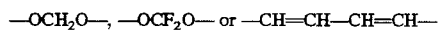

$R_4$, $R_5$, $R_6$, $R_7$ are each independently hydrogen, halogen, CN or $NO_2$; and W is O or S which comprises reacting an aminonitrile of formula III

(III)

wherein R is as described above with a perfluoroacylating agent of formula IV

(IV)

wherein m is an integer of 1 or 2, X is $OR_1$, Cl or O and $R_1$ is hydrogen or $C_1$–$C_6$alkyl with the proviso that when X is O, m must be 2 and when X is Cl or $OR_1$, then m must be 1 in the presence of a solvent, optionally in the presence of a base, to form a perfluoro-alkanoyl aminonitrile intermediate of formula I

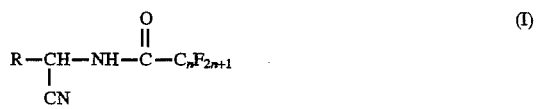

(I)

and cyclizing the formula I intermediate in the presence of an acid and at least one molar equivalent of water.

The 2-perfluoroalkyl-3-oxazolin-5-one compound is a key intermediate in the manufacture of insecticidal, acaricidal and nematicidal pyrrole compounds. The formula I perfluoroalkanoyl aminonitrile intermediate is described in co-pending patent application Ser. No. 08/175,845 filed concurrently herewith.

DETAILED DESCRIPTION OF THE INVENTION

Arylpyrrole compounds, particularly 2-aryl-5-trifluoromethylpyrrole-3-carbonitrile compounds are a new class of highly effective insecticidal, acaricidal and nematocidal agents. A key intermediate in their preparation is the 2-perfluoroalkyl-3-oxazolin-5-one compound of formula II

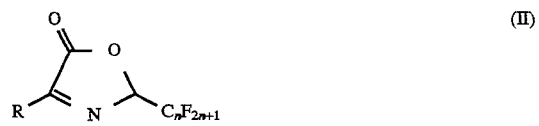

(II)

wherein n and R are as described hereinabove. Methods currently known to prepare the formula II oxazolinone involve the preparation of an appropriate arylglycine compound V via the hydrolysis of the aminonitrile III. The aminonitrile is obtained via the Strecker synthesis from the appropriate aldehyde precursor(W. L. Matier et al, J. Med. Chem.,1973, 16,901). Protection of the amino group in the aminonitrile III by acetylation to VI followed by acidic hydrolysis of both the cyano and the protecting groups is required due to the instability of the aminonitrile III under hydrolysis conditions. The thus-obtained glycine V is then trifluoroacetylated to give VII and cyclized to give the desired oxazolinone II in 4 steps. The reaction sequence is shown in flow diagram I, wherein R is p-chlorophenyl and n is 1.

FLOW DIAGRAM I

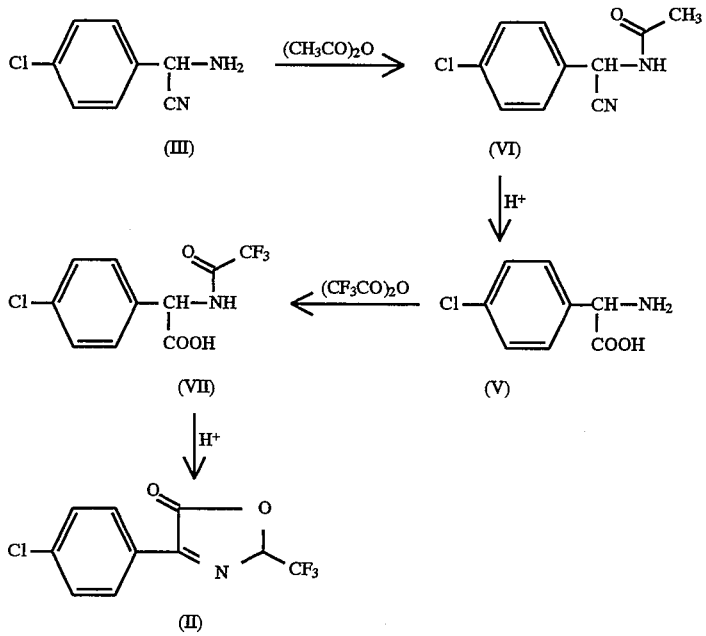

It has now been found that direct perfluoroacylation of the Strecker product III gives the perfluoroalkanoyl aminonitrile intermediate I which may be readily converted to the desired 2-perfluoroalkyl-3-oxazolin-5-one compound II. The reaction is shown in flow diagram II wherein m is 1 or 2, X is Cl OR$_1$ or O and R$_1$ is hydrogen or C$_1$–C$_6$alkyl with the proviso that when X is O, then m must be 2 and when X is Cl or OR$_1$, then m must be 1.

FLOW DIAGRAM II

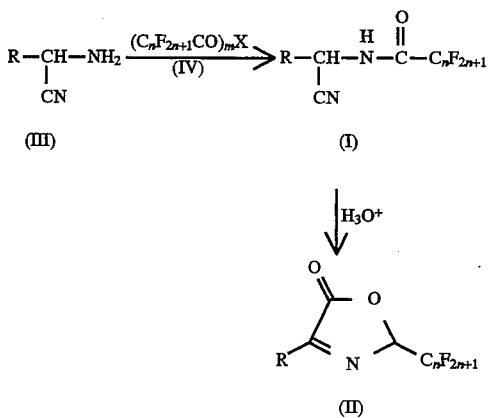

Surprisingly, the perfluoroalkanoyl aminonitrile of formula I may be cyclized in a single step in good yield under aqueous acid conditions to the 2-perfluoroalkyl-3-oxazolin-5-one compound of formula II.

Advantageously, the desired oxazolinone II may be obtained in just 2 steps from the Strecker product aminonitrile III.

Preferred compounds of formula I are those wherein n is 1, 2 or 3, more preferred are those wherein n is 1. Also preferred are those compounds of formula I wherein R is phenyl optionally substituted with one to three halogen, NO$_2$, C$_1$–C$_4$haloalkyl or C$_1$–C$_4$haloalkoxy groups.

In accordance with the method of invention, an aminonitrile of formula III is admixed with approximately an equimolar amount of a perfluoro-acylating agent of formula IV in the presence of a solvent, optionally in the presence of a base, to form the perfluoroalkanoyl aminonitrile of formula I. The formula I compound is then cyclized in the presence of an aqueous acid to form the formula II compound, 2-perfluoroalkyl-3-oxazolin-5 one.

Solvents suitable for use in the method of invention are aromatic hydrocarbons, or halogenated aromatic hydrocarbons, preferably aromatic hydrocarbons such as toluene, benzene, xylene and the like, more preferably, toluene.

Acids suitable for use in the method of invention include sulfuric acid, methanesulfonic acid, benzenesulfonic acid, p-toluenesulfonic acid, naphthlenesulfonic acid, fluoroboric acid, boron trifluoride complexes and the like. Boron trifluoride complexes may include BF$_3$ etherate, BF$_3$ methanol complex, BF$_3$ ethanol complex, BF$_3$ dihydrate and the like. Water may be introduced as a hydrate, i.e. p-toluensulfonic acid monohydrate or as a solute such as 30%–60% aqueous sulfuric acid.

In actual practice, if a perfluoroacyl chloride, such as trifluoroacetyl chloride, is used as the formula IV reagent, then an equimolar amount of a base may be added as an HCl scavenger. Among the bases which may be used are alkali metal carbonates or bicarbonates or mixtures thereof or tertiary amines. Alkalai metal carbonates such as sodium carbonate or potassium carbonate are contemplated as are bicarbonates such as sodium or potassium bicarbonate.

Tertiary amines suitable for use in the method of invention include any trisubstituted amine know in the art such a trialkylamine, dialkylarylamine, triarylamine, and the like preferably trialkylamine, more preferably triethylamine.

In order to provide a more clear understanding of the invention, the following examples are set forth below. These examples are merely illustrative and are not to be understood to limit the scope or underlying principles of the invention in any way.

EXAMPLE 1

Preparation of N-[(p-Chlorophenyl)cyanomethyl]-2,2,2-trifluoroacetamide

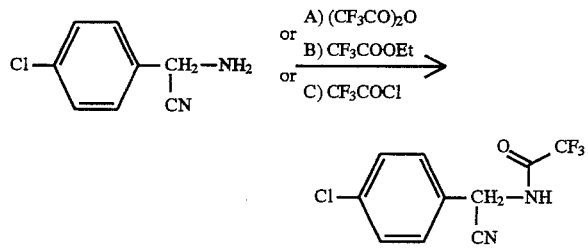

Method A: A stirred slurry of α-cyano-p-chlorobenzylamine (250 g, 1.5 mol) in toluene is treated with trifluoroacetic anhydride (315 g, 1.5 mol) at 35° C. over a 90 minute period. The mixture is treated with heptane, the resultant precipitate is filtered and the filter-cake is washed with toluene/heptane to give the title product, 323.7 g, 82% yield, mp 127°–128° C., identified by $^1$H, $^{13}$C and $^{19}$FNMR analyses.

Method B: A solution of α-cyano-p-chlorobenzylamine (83.3 g, 0.5 mol) in methanol is treated with ethyl trifluoroacetate (85.2 g, 0.6 mol), stirred at room temperature for about 16 hours and concentrated in vacuo to give a residue. The residue is crystallized from toluene/heptane to give the title product as a pale yellow solid, 88.3 g, 67.2% yield, mp 127°–128° C.

Method C: A mixture of α-cyano-p-chlorobenzylamine (83.3 g, 0.5 mol) and triethylamine (50.6 g, 0.5 mol) in toluene is treated dropwise with trifluoroacetyl chloride (66.2 g, 0.5 mol), stirred at ambient temperature for about 1 hour and filtered. The filtrate is washed once with water and concentrated in vacuo to give a residue. The residue is crystallized in toluene/hexane to give the title product, 114.2 g, 87% yield, mp 127°–128° C.

EXAMPLE 2

Preparation of N-(Arylcyanomethyl)-2,2,2-trifluoroacetamide

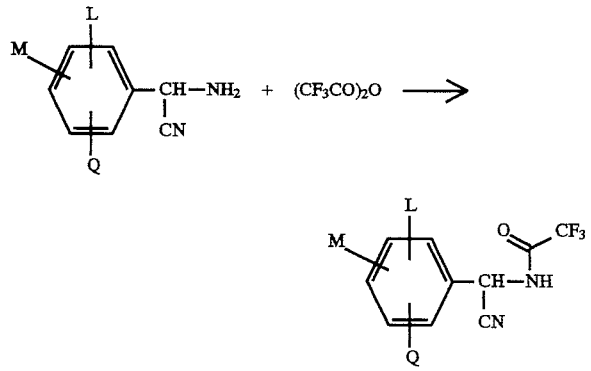

Using essentially the same procedure described as Method A in Example 1 and substituting the appropriate α-cyanobenzylamine as starting material, the following N-(arylcyanomethyl) 2,2,2-trifluoroacetamide products are obtained. The products are identified by $^1$H, $^{13}$C and $^{19}$FNMR analyses.

TABLE I

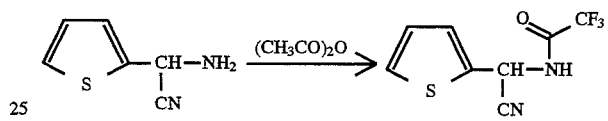

| L | M | Q | mp °C. | % Yield |
|---|---|---|---|---|
| H | 4-Br | H | 128.0–128.5 | 76 |
| H | 4-CF$_3$ | H | 115.0–116.0 | 63 |
| 3-Cl | 4-Cl | H | 113.0–115.0 | 35[a] |

[a]Based on aldehyde used in Strecker synthesis. (Crude Strecker product used as starting material)

EXAMPLE 3

Preparation of N-(α-Cyanothienyl)-2,2,2-trifluoroacetamide

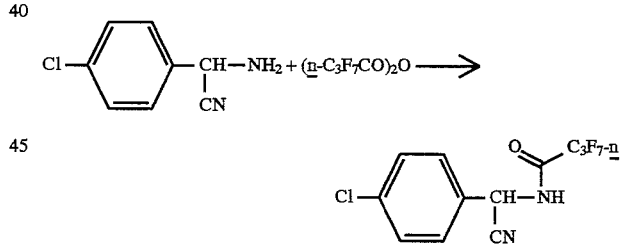

Using essentially the same procedure described as Method A in Example 1 and substituting the crude Strecker product, α-cyano-2-thiophenemethylamine, as starting material the title product is obtained in 23% yield[a], m.p. 73.0°–74.5° C., identified by $^1$H, $^{13}$C and $^{19}$FNMR analyses.

[a]Based upon starting aldehyde used in Strecker synthesis.

EXAMPLE 4

Preparation of N-[(p-Chlorophenyl)cyanomethyl]-2,2,3,3,4,4,4-heptafluorobutyramide

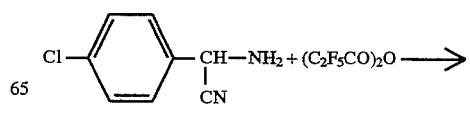

Using essentially the same procedure described as Method A in Example 1 and substituting heptafluorobutyric anhydride as the perfluoro-acylating agent, the title product is obtained as white crystals in 95% yield, mp 93.0°–95.0° C., identified by $^1$H, $^{13}$C and $^{19}$FNMR analyses.

EXAMPLE 5

Preparation of N-[(p-Chlorophenyl)cyanomethyl]-2,2,3,3,3-pentafluoropropionamide -continued

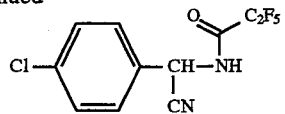

Using essentially the same procedure described as Method A in Example 1 and substituting pentafluoropropionic anhydride as the perfluoro-acylating agent, the title product is obtained as white crystals, 95% yield, mp 118.0°–118.5° C., identified by $^1$H, $^{13}$C and $^{19}$FNMR analyses.

EXAMPLE 6

Preparation of 4-(p-Chlorophenyl-2-(trifluoromethyl)-3-oxazolin-5-one

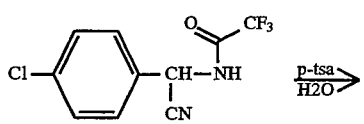

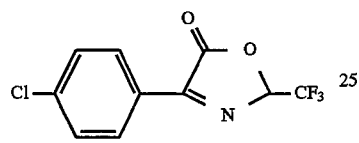

Method A: A solution of N-[(p-chlorophenyl) cyanomethyl]-2,2,2-trifluoroacetamide (0.1 mol) in toluene at 80° C. is treated portion-wise with p-toluene sulfonic acid monohydrate (p-tsa.H$_2$O)(0.11 mol) over an 0.75–1.0 hour period, stirred at 90°–95° C. for 2–3 hours, cooled and filtered. The filtrate is washed twice with water and concentrated in vacuo to give an oil residue. The oil is dissolved in heptane, filtered and the filtrate is vacuum distilled to give the title product as an oil, 55.6% yield, bp 78° C./0.01 mmHg, identified by $^1$H, $^{13}$C and $^{19}$FNMR analyses.

Method B: A solution of N-[p-(chlorophenyl) cyanomethyl]-2,2,2-trifluoroacetamide (26.3 g, 0.1 mol) in toluene and methanesulfonic acid (10.7 g, 0.11 mol) at 80° C. is treated with water (2 mL, 0.11 mol) over a 20 minute period, stirred at 90° C. for 8 hours and cooled. The reaction mixture is washed twice with water. The organic layer is concentrated in vacuo to give an oil which is vacuum distilled to give the title product as an oil 13.7 g, bp 80° C./0.01 mmHg.

EXAMPLE 7

Preparation of 4-(2-Thienyl-2-(trifluoromethyl)-3-oxazolin-5-one

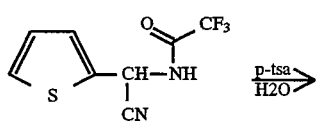

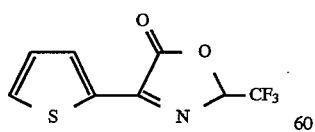

Using essentially the same procedure described as Method A in Example 6 and substituting N-(α-cyanothienyl)-2,2,2-trifluoroacetamide as starting material, the title product is obtained as a pale brown solid, 50% yield, mp 62.0°–65.0° C., identified by IR and $^1$H, $^{13}$C and $^{19}$FNMR analyses.

EXAMPLE 8

Preparation of 2-perfluoroalkyl-3-oxazolin-5-one

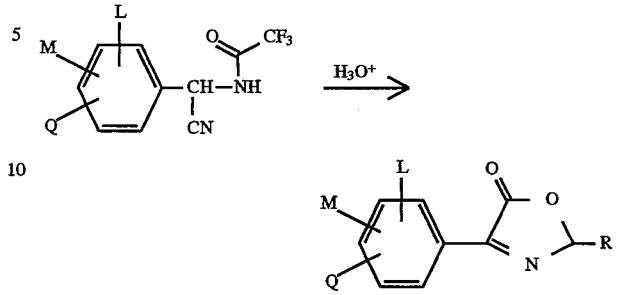

Using essentially the same procedure described as Method A in Example 6 and substituting the appropriate perfluoroalkyanoyl aminonitrile as starting material, the compounds shown in Table II are obtained.

TABLE II

| L | M | Q | R | mp °C. | % Yield |
|---|---|---|---|---|---|
| H | 4-Br | H | CF$_3$ | 48.0–51.0 | 64 |
| H | 4-CF$_3$ | H | CF$_3$ | 39.0–40.5 | 55 |
| 3-Cl | 4-Cl | H | CF$_3$ | 103°/0.1 mm$^a$ | 54 |
| H | 4-Cl | H | C$_2$F$_5$ | 39.0–42.0 | 72 |
| H | 4-Cl | H | n-C$_3$H$_7$ | 93.0–95.0 | 56 |

$^a$bp °C.

I claim:

1. A process for the preparation of a compound of formula II

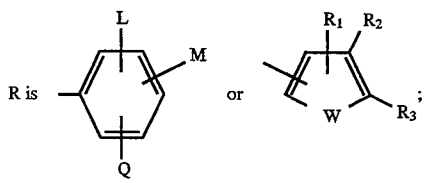

wherein n is an integer of 1, 2, 3, 4, 5, 6, 7 or 8;

R is

L is hydrogen or halogen;

M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$alkyl-sulfinyl or when M and Q are on adjacent positions they may be taken together with the carbon atoms to which they are attached to form a ring in which MQ represents the structure —OCH$_2$O—, —OCF$_2$O— or —CH=CH—CH=CH— with the proviso that at least one of L, M and Q must be other than hydrogen;

$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

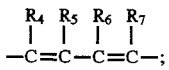

$R_4$, $R_5$, $R_6$ and $R_7$ are each independently hydrogen, halogen, CN or $NO_2$; and W is O or S which comprises reacting an aminonitrile of formula III

wherein R is as described above with a perfluoroacylating agent of formula IV

wherein m is an integer of 1 or 2, X is $OR_1$, Cl or O and $R_1$ is hydrogen or $C_1$-$C_6$alkyl with the proviso that when X is O, m must be 2 and when X is Cl or $OR_1$, then m must be 1 in the presence of a solvent, optionally in the presence of a base, to form a perfluoroalkanoyl aminonitrile intermediate of formula I

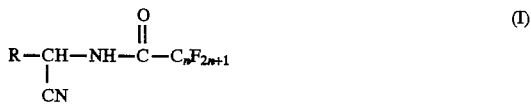

and reacting the formula I intermediate in the presence of an acid with at least one molar equivalent of water.

2. The process according to claim 1 wherein the perfluoroacylating agent of formula IV is

3. The process according to claim 2 wherein n is an integer of 1, 2 or 3.

4. The process according to claim 1 wherein the perfluoroacylating agent of formula IV is

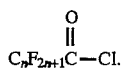

5. The process according to claim 4 wherein a base is present.

6. The process according to claim 5 wherein the base is sodium or potassium carbonate.

7. The process according to claim 5 wherein the base is a tertiaryamine.

8. The process according to claim 7 wherein the tertiary amine is a trialkylamine.

9. The process according to claim 8 wherein the trialkylamine is triethylamine.

10. The process according to claim 1 wherein the solvent is an aromatic hydrocarbon or a halogenated aromatic hydrocarbon.

11. The process according to claim 10 wherein the solvent is toluene.

12. The process according to claim 1 wherein the acid is sulfuric acid, methanesulfonic acid, benzenesulfonic acid, p-toluenesulfonic acid, naphthalenesulfonic acid, fluoroboric acid or a boron trifluoride complex.

13. The process according to claim 12 wherein the acid is p-toluenesulfonic acid.

14. The process according to claim 11 wherein the formula IV acylating agent is $(CF_3CO)_2O$.

15. The process according to claim 14 wherein the acid is p-toluenesulfonic acid.

16. A process for the preparation of a compound of formula II

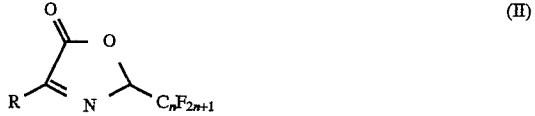

wherein n and R are as defined in claim 1 which comprises cyclizing a compound of formula I

in the presence of an acid and at least one molar equivalent of water.

17. The process according to claim 16 wherein the acid is sulfuric acid methanesulfonic acid, benzenesulfonic acid, p-toluenesulfonic acid, naphthalenesulfonic acid, fluoroboric acid or a boron trifluoride complex.

* * * * *